United States Patent [19]

Bowlin et al.

[11] Patent Number: 5,002,879

[45] Date of Patent: Mar. 26, 1991

[54] TREATMENT OF TUMORS WITH AUTOLOGOUS LAK CELLS, INTERLEUKIN-2 AND AN ORNITHINE DECARBOXYLASE INHIBITOR

[75] Inventors: Terry L. Bowlin, Maineville; Sai P. Sunkara, Cincinnati, both of Ohio

[73] Assignee: Merrell Dow Pharmaceuticals, Cincinnati, Ohio

[21] Appl. No.: 449,288

[22] Filed: Dec. 5, 1989

Related U.S. Application Data

[63] Continuation of Ser. No. 271,371, Nov. 14, 1988, abandoned, which is a continuation of Ser. No. 860,166, May 6, 1986, abandoned.

[51] Int. Cl.$^5$ .................. C12P 21/00; C12N 5/06; A61K 45/05
[52] U.S. Cl. .................. 435/71.1; 435/240.2; 424/93; 424/534; 424/85.2
[58] Field of Search ............ 435/71.1, 240.2; 424/85.2, 93, 534; 530/351

[56] References Cited

U.S. PATENT DOCUMENTS 4,499,072 2/1985 Sunkara et al. ............ 424/85.2
4,690,915 9/1987 Rosenberg ................ 514/2

OTHER PUBLICATIONS

Bowlin et al., Immunopharmacology 13(2) 1987, pp. 143–148.

*Primary Examiner*—Jacqueline Stone
*Attorney, Agent, or Firm*—Stephen L. Nesbitt

[57] ABSTRACT

Ornithine decarboxylase inhibitors when administered in conjunction with autologous LAK cells and interleukin-2 provide for an enhanced treatment of neoplastic disease states. This enhancement is provided by the ability of an ornithine decarboxylase inhibitor to reduce tumor load and to enhance interleukin-2 production in T helper cells.

2 Claims, 1 Drawing Sheet

TREATMENT OF TUMORS WITH AUTOLOGOUS LAK CELLS, INTERLEUKIN-2 AND AN ORNITHINE DECARBOXYLASE INHIBITOR

This is a continuation of application Ser. No. 271,371, filed Nov. 14, 1988, which is a continuation of Ser. No. 860,166, filed May 6, 1986, now abandoned.

BACKGROUND OF THE INVENTION

Neoplastic disease states are widespread and affect a significant portion of the population. These disease states are the subject of intensive research efforts. Unfortunately, despite such efforts and despite some modest successes, the overall control of these disease states has not been satisfactory. Recently a remarkable success was achieved when patients with advanced metastatic cancers were treated with autologous lymphokine-activated killer (LAK) cells and a recombinant-derived lymphokine, interleukin-2. Substantial tumor regression occurred in almost one-half of the patients treated, with complete remission reported in one instance lasting for at least ten months after cessation of therapy. Partial, but less complete, success was achieved in almost all of the other patients treated. Such success is especially significant because the tumors in the treated patients had resisted all previous conventional therapies.

While the success achieved by such therapy is encouraging, the procedure suffers from numerous practical limitations. In particular it is inordinantly expensive, even by the standards of conventional cancer therapy. The expense results primarily from its time consuming nature, requiring weeks of intensive-care and also from the high cost of interleukin-2. In addition, patients undergoing such therapy suffer from numerous, significant, and severe side effects, most notably massive fluid retention, respiratory complications, blood pressure variations and fever.

Applicants have discovered that if an ornithine decarboxylase inhibitor is administered to a patient prior to removal of lymphocytes, during incubation of the lymphocytes with interleukin-2, and also upon administration of the autologous LAK cells and interleukin-2, the therapy is both more effective and requires lesser quantities of the very costly interleukin-2. This improvement results in part from the known ability of an ornithine decarboxylase inhibitor to reduce tumor load, that is to slow down or temporarily arrest tumor growth, but also, from the ability of ornithine decarboxylase inhibitors to enhance interleukin-2 production by helper T cells. The use of applicants' improved therapy is expected to significantly reduce the incidence of untoward side effects and to reduce the cost of this therapy by allowing for the use of lesser amounts of interleukin-2.

SUMMARY OF THE INVENTION

This invention relates to an improved method of treating neoplastic disease states by systemic administration of autologous LAK cells and interleukin-2 which comprises the conjunctive administration of an ornithine decarboxylase inhibitor. Alpha-difluoromethyl ornithine (DFMO) is the preferred ornithine decarboxylase inhibitor.

DETAILED DESCRIPTION OF THE INVENTION

Figure 1:
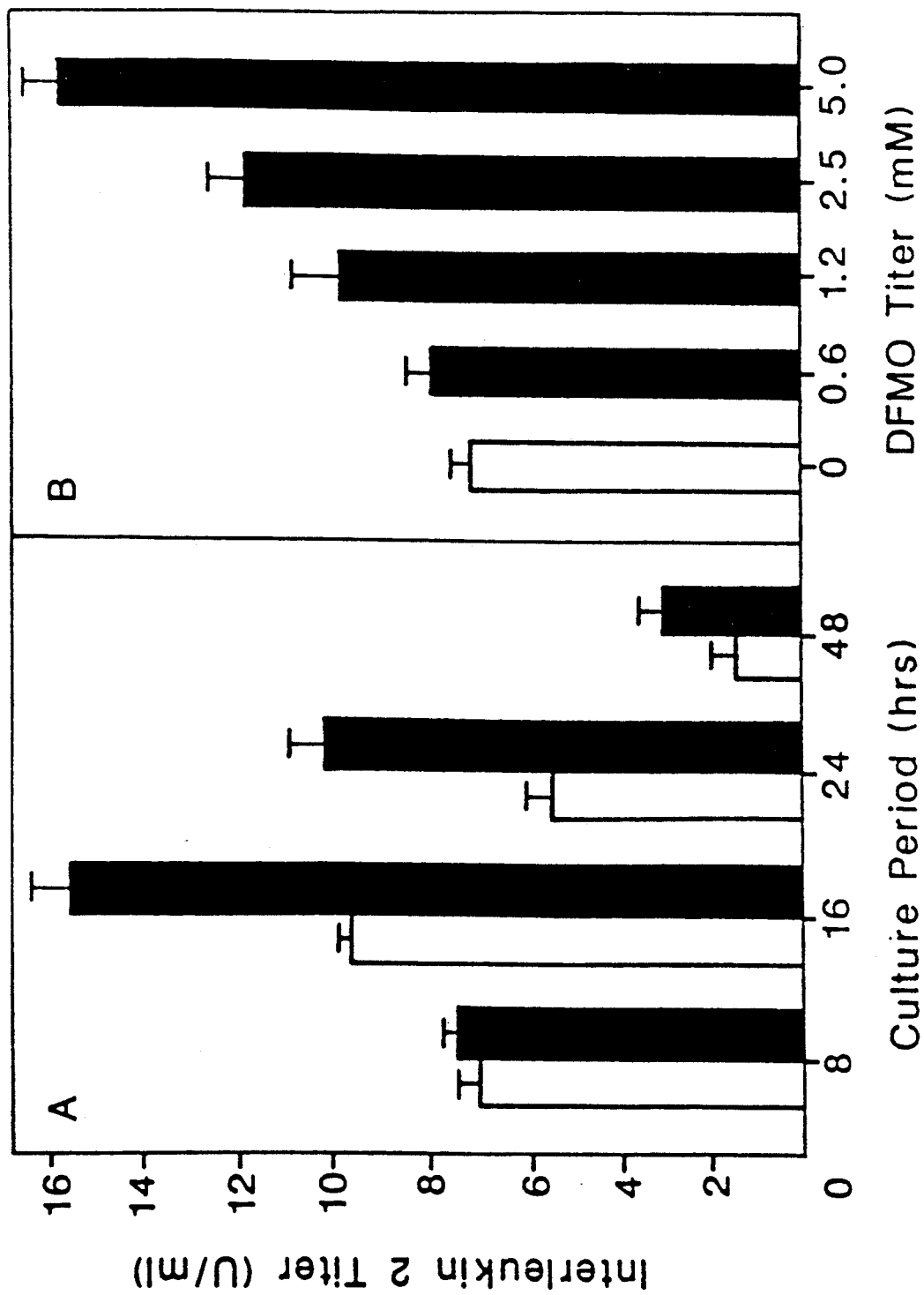

Ornithine decarboxylase is the enzyme which catalyzes the decarboxylation of ornithine to putrescine. Ornithine decarboxylase inhibitors are the those substances which substantially slow down this decarboxylation or eliminate it altogether. As used herein the term "ornithine decarboxylase inhibitor" or "ODC inhibitor" is taken to mean any such substance, although irreversible ODC inhibitors are preferred. In the practice of the present invention those irreversible ornithine decarboxylase inhibitors which are preferred are methyl acetylenic putrescine and compounds of the formulae

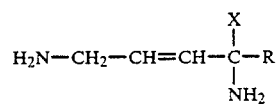

and

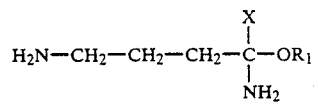

wherein
X is —CHF$_2$ or —CH$_2$F,
R is H or —COR$_1$, and
R$_1$ is —OH or a C$_1$-C$_6$ lower alkoxy groups
and the pharmaceutically acceptable salts thereof. Preferably, the ornithine decarboxylase inhibitors of this invention will be the methyl and ethyl esters of monofluoromethyl dehydroornithine, and the R,R-isomer of methyl acetylenic putrescine (i.e., (2R, 5R)-6-heptyne-2,5-diamine). Most preferably the ornithine decarboxylase inhibitor of this invention will be alpha-difluoromethyl ornithine (DFMO).

The ability of compounds to irreversibly inhibit ornithine decarboxylase in vivo can be demonstrated as follows: An aqueous solution of the appropriate compound is given orally or parenterally to male mice or rats. The animals are sacrificed 1 to 48 hours after administration of the compound, and the ventral lobes of the prostate removed and homogenized. The activity of ornithine decarboxylase is measured as generally described by E. A. Pegg and H. G. Williams-Ashman, *Biochem. J.* 108, 533-539 (1968).

The decarboxylation of ornithine to putrescine is the first step in the biosynthesis of the polyamines known as spermidine and spermine. Spermidine is formed by the transfer of an activated aminopropyl moiety from S-adenosyl S-methyl homocysteamine to putrescine, while spermine is formed by the transfer of a second aminopropyl group to spermidine. S-adenosyl S-methyl homocysteamine is formed by the decarboxylation of S-adenosylmethionine (SAM), a reaction catalyzed by the enzyme S-adenosylmethionine decarboxylase (SAM-DC). Since putrescine is a precursor of the polyamines, it is seen that blockade of the conversion of ornithine to putrescine, such as by inhibition of ODC, can provide a method for regulating the cellular levels of the polyamines.

The polyamines, which are found in animal tissues and microorganisms, are known to play an important role in cell growth and proliferation. The induction of cell growth and proliferation is associated with a marked increase in ODC activity and an increase in the levels of putrescine and the polyamines. Although the exact mechanism of the role of the polyamines in cell growth and proliferation is not known, it appears that the polyamines may facilitate macromolecular processes such as DNA, RNA, or protein synthesis. Polyamine levels are known to be high in the testes, ventral prostate, and thymus; in psoriatic skin lesions; and in other cells undergoing rapid growth processes.

It is also well known that the rapid proliferation of tumor tissue is marked by an abnormal elevation of polyamine levels. Hence, the polyamines may play an important role in the maintenance of tumor growth. It is thus believed that the ODC inhibitors may exert their therapeutic effect by blocking the formation of the polyamines and thereby slowing, interrupting, or arresting the proliferation and metastases of the tumor tissue.

In addition to the rather recent discovery concerning the use of irreversible inhibitors of ornithine decarboxylase, particularly with such compounds as alphadifluoromethyl ornithine, the methyl and ethyl esters of monofluoromethyl dihydroornithine, the R,R-isomer of methyl acetylenic putrescine, and the like, combinations of these ODC inhibitors with chemical cytotoxic agents has also shown promise in the treatment of diseases characterized by the rapid proliferation of tumor growth. Indeed, in the treatment of a malignant neoplastic disease, it has been reported that alphahalomethyl ornithines capable of irreversible ODC inhibition, in combination with known cytotoxic agents has demonstrated some synergistic effects in the treatment of such disease states.

Lymphokines are those substances produced by certain white blood cells or lymphocytes known as helper T-cells which activate various other lymphocytes. One such lymphokine is known as T-cell growth factor or interleukin-2. T-cell lymphocytes, once activated by antigen, will divide if interleukin-2 is present. As used herein, the term "interleukin-2" includes not only that produced naturally by helper T-cells, but also and more preferably recombinant derived interleukin-2 and certain of its muteins which are, for example, described in U.S. Pat. No. 4,518,584. Preferably, when the patient to be treated by the method of this invention is a human, the interleukin-2 will be recombinant interleukin-2 having the natural sequence of human interleukin-2 .

The use of autologous LAK cells and interleukin-2 to treat neoplastic disease states is known. See S. A. Rosenberg et al., *New England Journal of Medicine*, 313(23), 1485–92 (1985). This procedure can be performed by repeated lymphocytophereses in the usual manner in order to collect between $1 \times 10^8$ and $1 \times 10^{11}$, preferably between $1 \times 10^9$ and $1 \times 10^{11}$ mononuclear cells per patient.

In general, any effective amount of LAK cells are administered to the patient together with any effective amount of interleukin-2. Administration is intravenously, although it is preferable to administer additional interleukin-2 by bolus injection. The LAK cells are administered preferably once every day or every other day for from one to five daily doses. Generally, administration of the first daily dose begins about four days after the patient first undergoes leukapheresis to collect the cells for activation with interleukin-2. The quantity of LAK cells to be administered varies with the patient and the responsiveness of the neoplastic disease state to the treated. Generally, all of the cells which were removed and activated are administered depending upon the tolerance of the patient to the therapy. Preferably from $5 \times 10^8$ to $1 \times 10^{10}$ more preferably from 1. to $1.5 \times 10^9$ LAK cells are administered daily to the patient on each of three days over a period of from 3 to 10 days. Such a regimen will take about ten days and a patient may require from one to four such regimens sequentially.

Interleukin-2 to be administered intravenously can be formulated in, for example, normal saline. Intravenous doses of interleukin-2 are infused slowly, preferably over a period of from 5 to 60 minutes preferably about 15 minutes, for example, from two to six times a day, preferably three times a day beginning at the time of the first administration of LAK cells. Typically, a patient will receive from 10 to 100, preferably 20 to 50 such intravenous infusions during each course of therapy and such infusions will continue for from one to 10 preferably two to five days after the last administration of LAK cells. Bolus injections of interleukin-2 can optionally be administered to prolong the required, elevated serum levels. Preferably each bolus will contain from 1000 to 500,000, more preferably 10,000 to 100,000 units of interleukin-2 per kilogram of patients body weight and will be administered from two to six, preferably three times each day beginning with the first administration of LAK cells and again continuing from one to ten, preferably, two to five days after the last administration of LAK cells. Occasional doses of interleukin-2 may be omitted if the patient responds unfavorably.

The LAK cells are cultured by treating a patient's mononuclear lymphocytes with interleukin-2. The mononuclear lymphocytes are obtained by repeated lymphocytaphereses preferably with a continuous-flow cell separator collecting from $1 \times 10^8$ to $1 \times 10^{11}$, preferably $5 \times 10^9$ to $5 \times 10^{10}$ mononuclear cells per procedure. Preferably a patient will undergo such lymphocytapherses once each day for from one to five days. The lymphocytes can then be separated from the collected mononuclear cells using any established procedure, for example, with use of Ficall-Hypaque density gradients. The resulting mononuclear lymphocytes are then suspended in any appropriate media such as RPMI-1640 (low endotoxin [Microbiological Associates, Rockville, Md.]), which contains 10 units of penicillin per milliliter, 10 mg of streptomycin sulfate per milliliter, 2 mmol of glutamine per liter, 5 mg of gentamicin sulfate per milliliter, and two percent heat-inactivated human AB serum. Interleukin-2 is then added to the suspension of mononuclear lymphocytes and then incubated for from three to four days at, for example, 37° C. after which the resulting LAK cells were isolated and suspended with interleukin-2 in a media suitable for intravenous infusion into the patient to be treated wuch as in 0.9 percent sodium chloride containing five percent normal human serum albumin.

As pharmacologically useful agents, the ODC inhibitors can be administered in various manners to the patient being treated to achieve the desired effect. The compounds can be administered either alone or in combination with one another, or they can be administered in the form of pharmaceutical compositions, which are well known in the art. The compounds may be administered orally or parenterally, for example, intravenously, intraperitoneally, or subcutaneously, including injection of the active ingredient directly into the tumor.

The amount of ornithine decarboxylase inhibitor administered will vary over a wide range and can be any effective amount which will reduce tumor burden and enhance the production of interleukin-2 from activated LAK cells. Depending upon the patient to be treated, the severity of the condition being treated, the mode of administration, and the particular compound employed, the effective amount of compound administered will vary from about 10 mg/kg to 200 mg/kg of body weight of the patient per day. For example, a typical unit dosage form may be a tablet containing from 100 to 500 mg of a compound which may be administered to the patient being treated 1 to 10 times daily to achieve the desired effect.

The solid unit dosage forms can be of the conventional type. Thus, the solid form can be a capsul which can be of the ordinary gelatin type containing a novel compound of this invention and a carrier, for example, lubricant and inert fillers, such as lactose, sucrose and corn starch. In another embodiment, the novel compounds are tableted with conventional tablet bases such as lactose, sucrose or corn starch in combination with binders such as acacia, corn starch or gelatin, disintegrating agents such as corn starch, potato starch, or alginic acid, and a lubricant such as stearic acid, or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions ethanols and glycols such as propylene glycol or polyethylene glycol are preferred liquid carriers, particularly for injectable solutions.

As used herein, the term "conjunctive administration" when used in relation to the administration of an ornithine decarboxylase inhibitor means the administration of an the lymphocytes are incubated with interleukin-2, and upon administration of the activated, autologous LAK cells and interleukin-2.

The ability of an ornithine decarboxylase inhibitor to enhance interleukin-2 production from T-cells can be illustrated by the following:

EXAMPLE 1

Effect of In Vitro DFMO and putrescine treatment on IL2 production and Polyamine Biosynthesis Splenic T cells were obtained by the nylon wool column method of Julius et al. *Eur. J. Immunol.* 3, 645 (1973), and stimulated with 2.5 g/ml concanavalin A (Con A) in RPMI-1640 culture medium supplemented with 10% fetal calf serum (FCS) and $5 \times 10^5$ M 2-mercaptoethanol (2 me). Following incubation (37° C.) for various time periods these cells were then harvested, viability determined, and ODC and polyamine analysis performed. Supernatant fluids (SF) from these same cultures were extensively dialyzed and assayed for IL 2 activity. As illustrated in FIG. 1, SF derived from these same cultures showed increased levels of detectable IL 2 activity. DFMO enhanced IL 2 production (16 hr) in a dose-dependent manner. Peak IL 2 activity was detected 16 hrs following mitogen stimulation (FIG. 1) and as shown in Table 1 putrescine, spermidine and spermine levels were reduced 76, 67 and 27% respectively, following 16 hrs of DFMO treatment.

DFMO irreversibly inhibits the conversion of ornithine to putrescine. To establish if the effect of DFMO was specifically due to inhibition of polyamine biosynthesis, exogenous putrescine was added at the initiation of cell culture in combination with DFMO. As shown in Table 1, putrescine reversed the effect of DFMO on IL 2 production and polyamine biosynthesis in a dose-dependent manner. However, putrescine only negated the effect of DFMO when endogenous spermidine biosynthesis returned to control levels.

TABLE 1

| TREATMENT IN VITRO | POLYAMINE CONCENTRATION (PMOL/$10^6$ CELLS) | | | INTERLEUKIN 2 TITER (16 HR) (U/ml) |
|---|---|---|---|---|
| | PUTRESCINE | SPERMIDINE | SPERMINE | |
| Control | 8.2 ± 1.5 | 235.9 ± 10.3 | 291.0 ± 59.7 | 9.1 ± 0.1 |
| DFMO (2.5 mM) | 2.0 ± 0.5* | 157.4 ± 2.0* | 213.7 ± 44.5 | 13.9 ± 0.1* |
| Putrescine (50 μM) | 102.9 ± 5.1 | 257.7 ± 10.1 | 248.5 ± 36.4 | 8.8 ± 1.1 |
| DFMO (2.5 mM) + Putrescine (50 μM) | 86.9 ± 4.0+ | 244.2 ± 9.7+ | 233.0 ± 33.0 | 9.1 ± 0.1+ |
| DFMO (2.5)mM) + Putrescine (25 μM) | 60.3 ± 3.2+ | 342.4 ± 8.8+ | 255.3 ± 40.8 | 10.5 ± 0.3+ |
| DFMO (2.5 mM) + Putrescine (10 μM) | 14.7 ± 2.2+ | 164.6 ± 13.8 | 221.1 ± 19.8 | 15.5 + 0.7 |

*Significant compared with control (p < 0.001)
+Significant compared with DFMO (p < 0.01)
Table 1. Effect of in vitro DFMO and putrescine treatment on IL 2 production and polyamine biosynthesis. Stimulation of T cells and determination of IL 2 titers as indicated in figure 1. DFMO (2.5 mM) and putrescine were both present throughout the culture period (16 hr). Cell preparation for polyamine analysis by RP-HPLC was based on the dansylation procedure of Seiler, Meth. Biochem. Anal. 18, 259 (1970). RP-HPLC was performed on a Waters gradient HPLC system, equipped with two model 510 pumps, a model 680 automated gradient controller, a model 710B WISP Auto-injector, and a Resolve 5 C18 column. Data compiled from two separate experiments (means ± S.E.; n = 4).

EXAMPLE 2

Effect of In Vivo DFMO Treatment on IL 2 Production and Polyamine Levels

To evaluate the effect of DFMO administration in vivo on IL 2 production, C57BL/6 mice were treated with 2% DFMO in drinking water. Spleens were removed, single cell suspensions prepared, and erythrocytes lysed. Splenic leukocytes were then assayed for polyamines and a separate portion of cells stimulated with Con A. As shown in Table 2, in vivo DFMO treatment for six days reduced freshly isolated splenic leukocyte putrescine and spermidine levels. However, following mitogen stimulation, detectable levels of IL 2 activity were increased two-three fold in the DFMO treated groups. Combination treatment with DFMO and putrescine (50 mg/kg/day) in vivo reversed the effect of DFMO administration alone on IL 2 production, putrescine and spermidine levels by 60, 69 and 68% respectively.

TABLE 2

| TREATMENT IN VIVO | POLYAMINE CONCENTRATION (PMOL/10⁶ CELLS) | | | INTERLEUKIN 2 TITER (U/ml) | |
|---|---|---|---|---|---|
| | PUTRESCINE | SPERMIDINE | SPERMINE | 24 HR | 48 HR |
| Control | 9.5 ± 0.7 | 144.6 ± 3.2 | 155.6 ± 9.4 | 6.6 ± 0.6 | 1.1 ± 0.1 |
| DFMO (2%) | 5.3 ± 0.1* | 118.8 ± 4.4* | 189.3 ± 6.5 | 12.2 ± 1.1* | 4.2 ± 9.4* |
| Putrescine (50 mg/kg) | 15.8 ± 1.2 | 187.4 ± 9.6 | 188.0 ± 15.9 | 7.0 ± 0.4 | 1.5 ± 0.1 |
| DFMO + Putrescine | 7.8 ± 0.3+ | 136.5 ± 2.3+ | 168.9 ± 2.4 | 8.4 ± 0.7+ | 2.0 ± 0.2+ |

*Significant compared with control ($p < 0.001$)
+Significant compared with DFMO ($p < 0.01$)
Table 2. Effect of in vivo DFMO treatment on IL 2 production and polyamine levels. C57BL/6 mice received 2% DFMO in their drinking water (approximately 3 g/kg per day) continuously for 6 days and/or putrescine (50 mg/kg) i.p. for 5 days. Control group received normal drinking water. Spleens were removed, single cell suspensions prepared, and erythrocytes lysed. Fresh splenic leukocytes were asseyed for polyamines (see FIG. 1) and a separate portion of cells ($10^6$/ml) stimulated with Con A (2.5 μg/ml). IL 2 activity and polyamine levels were determined as described in Table 1. Data compiled from two separate experiments (mean ± S.E.; n = 4).

EXPLANATION OF FIG. 1

Effect of in vitro DFMO treatment of IL 2 production, in Con A stimulated murine T cell cultures T cells ($10^6$/ml) were incubated (37° C.) with Con A (2.5 g/ml) in the presence (solid bars) or absence (open bars) of DFMO (2.5 mM; Panel A). At various time points cells were harvested and viability determined. Supernatant fluids were extensively dialyzed and IL 2 activity was determined in proliferation ($[^3H]$-TdR incoropration) assays, utilizing the IL 2 dependent CTLL-20 cell line, by the method of Gillis et al., *J. Immunol* 120, 2027 (1978) Units of IL 2 activity were determined by regression analysis from complete titrations of the supernatant fluid. The reciprocal of the sample dilution providing 50% of the maximum CPM of a laboratory control IL 2 preparation represents the number of IL 2 units per ml. Data compiled from two separate experiments (mean ±S.E.; n=4).

What is claimed is:

1. In a process for preparing lymphokine activated killer cells for use in adoptive immunotherapy wherein a patient's T cells are incubated ex vivo in the presence of interleukin 2, the improvement which comprises conducting the ex vivo incubation in the presence of an interleukin 2 enhancing amount of an ornithine decarboxylase inhibitor.

2. The process of claim 1 wherein the ornithine decarboxylase inhibitor is difluoromethylornithine.

* * * * *

UNITED STATES PATENT AND TRADEMARK OFFICE
CERTIFICATE OF CORRECTION

PATENT NO.   : 5,002,879

DATED        : March 26, 1991

INVENTOR(S)  : Terry L. Bowlin and Sai P. Sunkara

It is certified that error appears in the above-identified patent and that said Letters Patent is hereby corrected as shown below:

Column 2, Line 6 patent reads: "are the those" and should read -- are those--.

Column 3, Line 68 patent reads: "treated" and should read --treatment--.

Column 4, Line 21 patent reads: "required, elevated" and should read --required or elevated--.

Column 4, Line 54 patent reads: "wuch" and should read --such--.

Column 5, Line 14 patent reads: "capsul" and should read --capsule--.

Column 5, Line 62 patent reads: "administration of an the lymphocytes are incubated" and should read --administration of an ornithine decarboxylase inhibitor during the time in which the lymphocytes are incubated--.

Column 7, Line 13 patent reads: "asseyed" and should read --assayed--.

Column 7, Line 21 patent reads: "At various time points cells" and should read --at various time points, cells--.

UNITED STATES PATENT AND TRADEMARK OFFICE
CERTIFICATE OF CORRECTION

PATENT NO. : 5,002,879

DATED : March 26, 1991

INVENTOR(S) : Terry L. Bowlin and Sai P. Sunkara

It is certified that error appears in the above-identified patent and that said Letters Patent is hereby corrected as shown below:

Column 7, line 27 patent reads: "(1978)" and should read --(1978).--.

Signed and Sealed this

Fifth Day of January, 1993

Attest:

DOUGLAS B. COMER

Attesting Officer

Acting Commissioner of Patents and Trademarks